US010254527B2

(12) United States Patent
Ueno (10) Patent No.: US 10,254,527 B2
(45) Date of Patent: Apr. 9, 2019

(54) OBSERVATION METHOD USING MICROSCOPIC IMAGING DEVICE (71) Applicant: Kabushiki Kaisha Toshiba, Minato-ku (JP)

(72) Inventor: Soichiro Ueno, Ota (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 570 days.

(21) Appl. No.: 14/811,067

(22) Filed: Jul. 28, 2015

(65) Prior Publication Data
US 2016/0033751 A1 Feb. 4, 2016

(30) Foreign Application Priority Data

Jul. 31, 2014 (JP) .................................. 2014-156706

(51) Int. Cl.
G02B 21/00 (2006.01)
G02B 21/36 (2006.01)
(Continued)

(52) U.S. Cl.
CPC .......... *G02B 21/365* (2013.01); *B01L 3/5085* (2013.01); *B01L 3/502715* (2013.01);
(Continued)

(58) Field of Classification Search
CPC ..... B01L 2300/0654; B01L 2300/0851; B01L 2300/0877; B01L 2300/0887;
(Continued)

(56) References Cited

U.S. PATENT DOCUMENTS 9,256,008 B2 2/2016 Haguet et al.
9,324,751 B2 4/2016 Taguchi
(Continued)

FOREIGN PATENT DOCUMENTS

CN 102792151 A 11/2012
CN 103154662 A 6/2013
(Continued)

OTHER PUBLICATIONS

Mohendra Roy, et al., "Low-cost telemedicine device performing cell and particle size measurement based on lens-free shadow imaging technology", Biosensors and Bioelectronics, 67, 2015, pp. 715-723.

*Primary Examiner* — Thanh Luu
(74) *Attorney, Agent, or Firm* — Oblon, McClelland, Maier & Neustadt, L.L.P.

(57) ABSTRACT

A certain embodiment provides an observation method using a microscopic imaging device which has a solid-state imaging device having a plurality of pixels arranged at predetermined intervals, each of the pixels including a microlens configured to collect light, and a light receiving unit configured to receive the light collected by the microlens. The observation method includes mounting an object to be observed on the microlenses or above the microlenses by disposing a specimen containing the object to be observed on the microscopic imaging device, and imaging the object to be observed, mounted on the microlenses or above the microlenses by a solid-state imaging device.

12 Claims, 10 Drawing Sheets

(51) Int. Cl.
- *G02B 27/00* (2006.01)
- *G02B 21/34* (2006.01)
- *H01L 27/146* (2006.01)
- *G01N 21/64* (2006.01)
- *B01L 3/00* (2006.01)
- *G02B 13/24* (2006.01)
- *G02B 3/00* (2006.01)

(52) U.S. Cl.
CPC ..... *G01N 21/6458* (2013.01); *G02B 21/0008* (2013.01); *G02B 21/34* (2013.01); *G02B 27/0025* (2013.01); *H01L 27/14601* (2013.01); *H01L 27/14627* (2013.01); *B01L 2300/0654* (2013.01); *B01L 2300/0851* (2013.01); *B01L 2300/0877* (2013.01); *B01L 2300/0887* (2013.01); *G02B 3/0056* (2013.01); *G02B 13/24* (2013.01)

(58) Field of Classification Search
CPC ............ B01L 3/502715; B01L 3/5085; G01N 21/6458; G02B 13/24; G02B 21/0008; G02B 21/34; G02B 21/365; G02B 27/0025; G02B 3/0056
See application file for complete search history.

(56) References Cited

U.S. PATENT DOCUMENTS

| | | | |
|---|---|---|---|
| 9,426,429 | B2 | 8/2016 | Zheng et al. |
| 2007/0207061 | A1 | 9/2007 | Yang et al. |
| 2007/0215793 | A1* | 9/2007 | Gruhlke ................ G06F 3/0421 250/221 |
| 2011/0181884 | A1 | 7/2011 | Cui et al. |
| 2011/0234757 | A1 | 9/2011 | Zheng et al. |
| 2012/0026093 | A1* | 2/2012 | Duparre .............. G06F 3/03547 345/166 |
| 2012/0098950 | A1 | 4/2012 | Zheng et al. |
| 2012/0142086 | A1 | 6/2012 | Haguet et al. |
| 2013/0293749 | A1 | 11/2013 | Vaartstra |
| 2014/0118590 | A1 | 5/2014 | Taguchi |
| 2014/0152801 | A1* | 6/2014 | Fine ................... G02B 21/0008 348/79 |

FOREIGN PATENT DOCUMENTS

| | | |
|---|---|---|
| JP | 10-307076 A | 11/1998 |
| JP | 2000-171401 | 6/2000 |
| JP | 2003-121756 | 4/2003 |
| JP | 2005-195492 A | 7/2005 |
| JP | 2012-118194 | 6/2012 |
| JP | 2012-529025 A | 11/2012 |
| JP | 2013-45857 A | 3/2013 |
| KR | 10-2012-0026581 A | 3/2012 |

* cited by examiner

OBSERVATION METHOD USING MICROSCOPIC IMAGING DEVICE

CROSS REFERENCE TO RELATED APPLICATIONS

This application is based upon and claims the benefit of priority from the prior Japanese Patent Application No. 2014-156706 filed in Japan on Jul. 31, 2014; the entire contents of which are incorporated herein by reference.

FIELD

Embodiments described herein relate generally to an observation method using a microscopic imaging device.

BACKGROUND

Generally, observation of an object to be observed using an optical microscope is performed as follows. First, the object to be observed is mounted on a stage portion. Next, light is irradiated to the object to be observed, and the light reflected from the object to be observed is collected by an observational optical system including an objective lens, an ocular lens, and the other lenses, and these lenses of the observational optical system are adjusted, respectively, to form an image to a desired position at a desired magnification. The thus formed image can be observed through an ocular lens for observation of the object to be observed.

As descried above, in such an observation method using the optical microscope, lenses of an observational optical system are need to be adjusted, respectively, so as to image light reflected from an object to be observed to a desired position at a desired magnification upon observation of the object to be observed. Further, the optical microscope has a fixed field of view, so that as the object to be observed is magnified, observation is made only a part of the object to be observed. Observation of the whole of the object to be observed requires full scan over the object to be observed for example while moving the object to be observed.

As described above, generally, complicated operation is required so as to observe the object to be observed using the optical microscope.

DESCRIPTION OF THE EMBODIMENTS

A certain embodiment provides an observation method using a microscopic imaging device which has a solid-state imaging device having a plurality of pixels arranged at predetermined intervals, each of the pixels including a microlens configured to collect light, and a light receiving unit configured to receive the light collected by the microlens. The observation method includes mounting an object to be observed on the microlenses or above the microlenses by disposing a specimen containing the object to be observed on the microscopic imaging device, and imaging the object to be observed, mounted on the microlenses or above the microlenses by a solid-state imaging device.

The observation methods according to embodiments, the methods using a microscopic imaging device, will be described below in detail with reference to figures.

Figure 1:
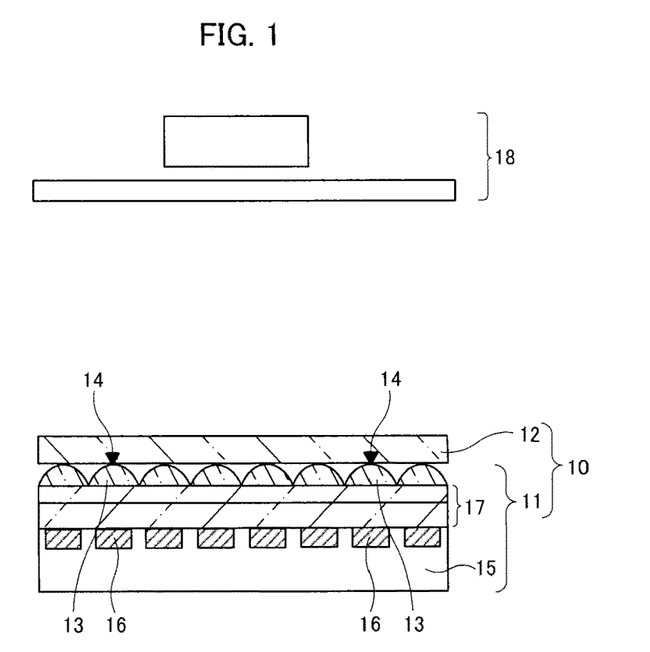
FIG. 1 is a cross-sectional view illustrating a microscopic imaging device used for an observation method according to an embodiment.

FIG. 1 is a cross-sectional view illustrating a microscopic imaging device used for the observation method according to the embodiment. The microscopic imaging device 10 illustrated in FIG. 1 includes the solid-state imaging device 11, and a stage portion 12 on which an object to be observed can be mounted.

The solid-state imaging device 11 has a sensor unit configured by arranging a plurality of pixels 14 at predetermined intervals. Each of the pixels 14 includes the microlens 13 for collecting light, and the light receiving unit for receiving light collected by the microlens 13. The solid-state imaging device 11 will be described below in detail.

In the solid-state imaging device 11 illustrated in FIG. 1, a plurality of photodiode layers 16 being impurity layers are formed to be arranged in a semiconductor substrate 15 including for example silicon. In the present embodiment, for example the photodiode layer 16 is defined as the light receiving unit, but the light receiving unit preferably receives and photoelectrically converts incident light, and not always need to employ the photodiode layer 16.

An intermediate layer 17 is provided on a surface of the semiconductor substrate 15 which has the plurality of photodiode layers 16. The plurality of microlenses 13 are formed to be arranged on a surface of the intermediate layer 17 so as to correspond to an arrangement of the plurality of photodiode layers 16.

The intermediate layer 17 is for example a wavelength selective layer such as a color filter layer, a planarization layer for making the surface of the intermediate layer flat, or the like.

The stage portion 12 for mounting thereon the object to be observed is provided on at least the sensor unit on the surface of the solid-state imaging device 11. The stage portion 12 is configured by a resin which has a translucency for transmitting light having a predetermined wavelength band (e.g., visible light) and has a refractive index different from that of the microlens 13 of the solid-state imaging device 11. The resin is glass, for example. The stage portion 12 may have a flat shape or may be a liquid or solid state embedded on the microlens 13.

The stage portion 12 is disposed on the plurality of microlenses 13 to make contact with the plurality of microlenses 13, and has a predetermined thickness. A thickness of the stage portion 12 will be described later.

In the microscopic imaging device 10 having such a configuration, the object to be observed can be observed by mounting the object to be observed on a surface of or on the inside of the stage portion 12 of the microscopic imaging device 10 which is disposed under a light source 18 and by imaging the object to be observed which is mounted as described above using the solid-state imaging device 11. It is noted that the light source 18 may be, for example, a lighting device such as a fluorescent lamp in a room in which the microscopic imaging device 10 is disposed or may be a dedicated imaging light source for imaging the object to be observed in detail.

Figure 2:
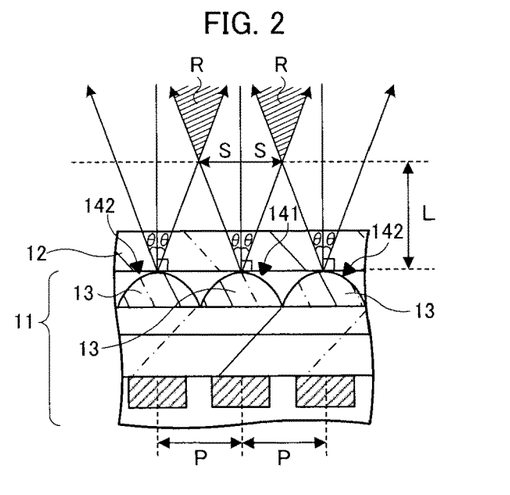
FIG. 2 is a diagram illustrating an enlarged portion of the microscopic imaging device of FIG. 1.

FIG. 2 is a diagram illustrating an enlarged portion of the microscopic imaging device 10 having been described above. The microscopic imaging device 10 will be described below in detail with reference to FIG. 2. The microscopic imaging device 10 can image the object to be observed which is mounted within a predetermined distance L from a top of the microlens 13. Here, the predetermined distance L represents a distance determined by a viewing angle θ of the microlens 13 of the solid-state imaging device 11, and an interval P between pixels 14 which the solid-state imaging device 11 has. The predetermined distance L will be described below.

When a distance of an imaging area of the object to be observed is denoted by S, and the interval between pixels 14 is denoted by P, as illustrated in FIG. 2, a condition in which the object to be observed can be normally imaged by the microscopic imaging device 10 is expressed as follows:

$$2 \times S \leq P \quad \text{(formula 1).}$$

Even if the distance S of the imaging area does not satisfy the formula 1, the microscopic imaging device 10 can image the object to be observed. However, when the distance S of the imaging area does not satisfy the formula 1, part of the object to be observed exists within a hatched area R in figure. When the object to be observed exists in the hatched area R, light reflected from the object to be observed is received by a pixel 141 originally configured to receive the light, and is also received by another pixel 142 adjacent to the pixel 141. Accordingly, the microscopic imaging device 10 cannot normally image the object to be observed and provides a so-called out-of-focus image.

Here, when the viewing angle of the microlens 13 is denoted by θ, and a distance from the top of the microlens 13 to the object to be observed is denoted by L, the distance S of the imaging area of the object to be observed is expressed as follows:

$$\tan \theta = S/L \quad \text{(formula 2)}$$

From formulas 1 and 2, the distance L from the top of the microlens 13 to the object to be observed is expressed as follows:

$$L \leq P/(2 \times \tan \theta) \quad \text{(formula 3)}$$

According to formula 3, the microscopic imaging device 10 according to the present embodiment can normally image the object to be observed which is mounted so that a distance L between the top of the microlens 13 and the object to be observed is not more than $P/(2 \times \tan \theta)$.

For example, when the following formulas are satisfied: interval P between pixels 14=1.76 μm (S=0.88 μm), θ=10 deg, the distance L is expressed as L≤5 μm. Accordingly, the microscopic imaging device 10 can normally image the object to be observed which is mounted so that a distance L between the top of the microlens 13 and the object to be observed is not more than 5 μm. Similarly, when the following formulas are satisfied: the interval P between pixels 14=3.52 μm (S=1.76 μm), θ=10 deg, the distance L is expressed as L≤10 μm. Accordingly, the microscopic imaging device 10 can normally image the object to be observed which is mounted so that a distance L between the top of the microlens 13 and the object to be observed is not more than 10 μm. When the following formulas are satisfied: interval P between pixels 14=17.64 μm (S=8.82 μm), θ=10 deg, the distance L is expressed as L≤50 μm. Accordingly, the microscopic imaging device 10 can normally image the object to be observed which is mounted so that a distance L between the top of the microlens 13 and the object to be observed is not more than 50 μm.

As described above, the microscopic imaging device 10 used for the observation method according to the present embodiment can normally image the object to be observed which is mounted so that a distance L between the top of the microlens 13 and the object to be observed is not more than $P/(2 \times \tan \theta)$. Accordingly, in order to normally observe the object to be observed which is disposed on the surface of the stage portion 12, the stage portion 12 needs to have a thickness of at least not more than $P/(2 \times \tan \theta)$. Further, when the object to be observed is on the inside of the stage portion 12, the object to be observed which is mounted so that a distance L between the top of the microlens 13 and the object to be observed is not more than $P/(2 \times \tan \theta)$ can be normally imaged.

Figure 3:
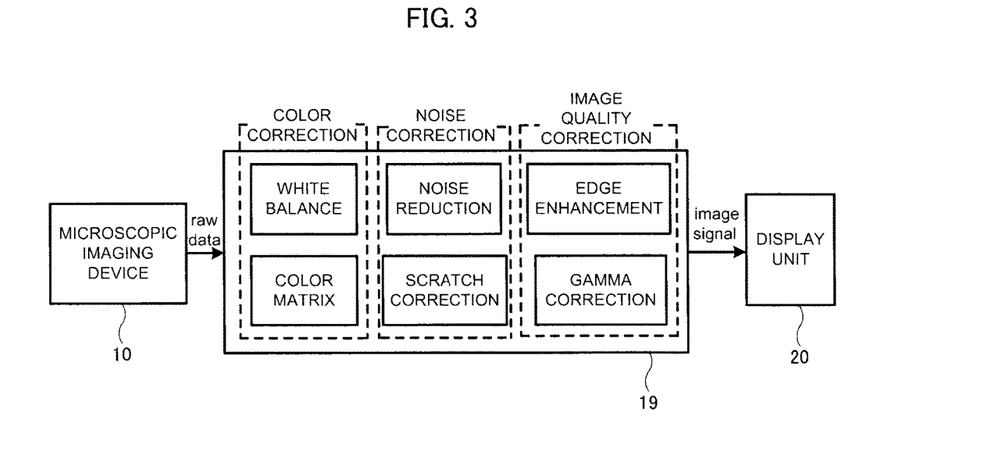
FIG. 3 is a schematic electrical block diagram illustrating an observation system using the microscopic imaging device of FIG. 1.

FIG. 3 is a schematic electrical block diagram illustrating an observation system using the microscopic imaging device 10 having been described above. The observation system illustrated in FIG. 3 includes the microscopic imaging device 10, a logic circuit portion 19 as a signal processing circuit, and a display unit 20.

The logic circuit portion 19 performs, on a voltage signal (raw data) obtained from the microscopic imaging device 10, predetermined signal processing such as color correction (white balance, color matrix), noise correction (noise reduction, scratch correction), image quality correction (edge enhancement, gamma correction), and outputs, as an image signal, the voltage signal subjected to the signal processing. In the present embodiment, the microscopic imaging device 10 does not include an observational optical system such as a lens for forming an image, or a lens for magnification or reduction, so that the logic circuit portion 19 does not include a correction circuit for correction of aberration of such a lens, or shading correction.

The logic circuit portion 19 may be included in the solid-state imaging device 11, for example, by being provided on the semiconductor substrate 15 around a sensor unit 22 (FIG. 4A) being an area in which the pixels 14 are arranged, or may be a component separate from the solid-state imaging device 11 provided separately from the solid-state imaging device 11.

Next, the display unit 20 is for example a display device, and the display unit 20 forms an image of the object to be observed based on the image signal output from the logic circuit portion 19, and displays the image thereon. The display unit 20 can wholly display the object to be observed at once which is mounted on the stage portion 12 of the microscopic imaging device 10.

The observation system can wholly displays, on the display unit 20, the object to be observed at once which is mounted on the stage portion 12 of the microscopic imaging device 10. Accordingly, the whole of the object to be observed can be simultaneously observed in real time.

Figure 4A:
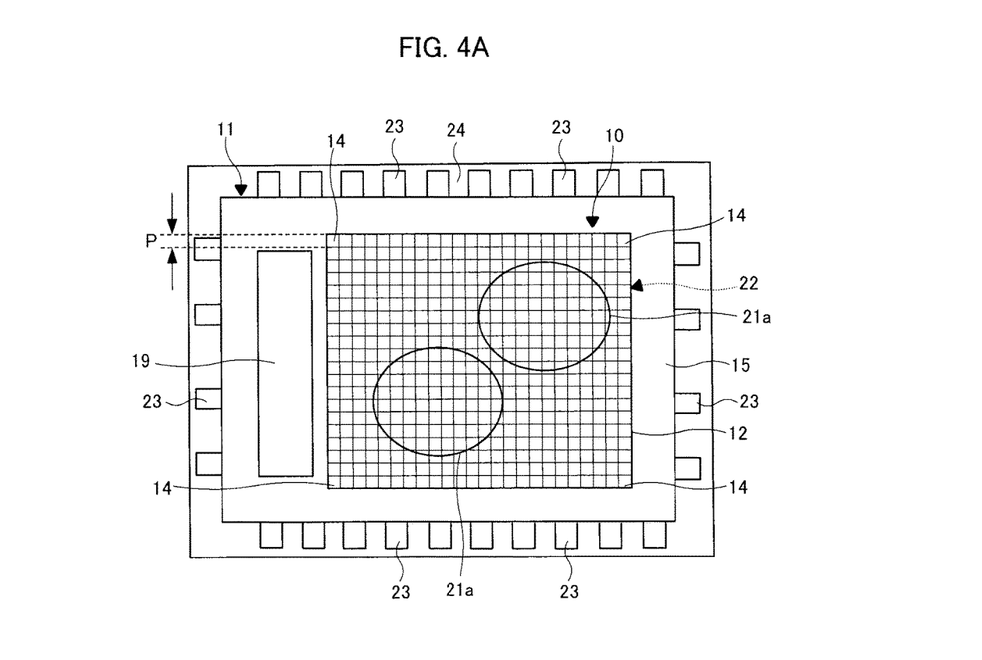
FIG. 4A is a top view of a microscopic imaging device having a stage portion on which an object to be observed is mounted.
Figure 4B:
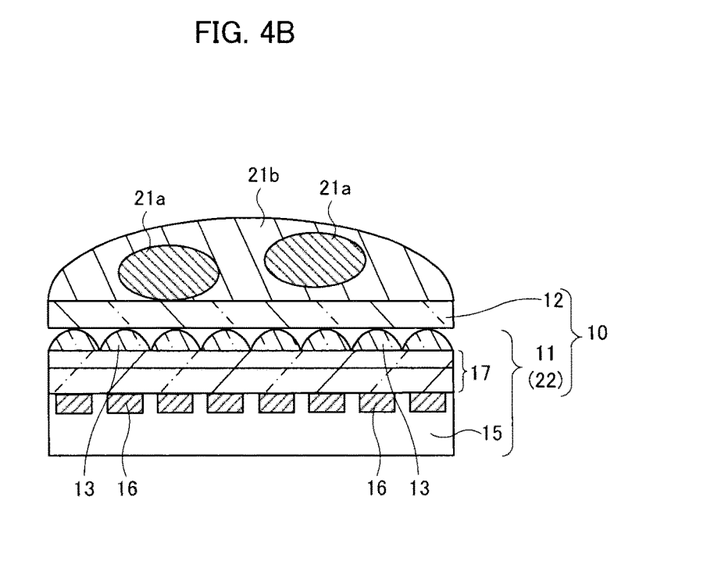
FIG. 4B is a partial cross-sectional view of FIG. 4A.

Next, the observation method according to the embodiment, the method using the microscopic imaging device 10 having been described above, will be described. First, as illustrated in FIGS. 4A and 4B, a specimen is mounted on the surface of the stage portion 12 of the microscopic imaging device 10 (above the microlens 13 of the microscopic imaging device 10) disposed under a desired light source 18. In the present embodiment, the specimen is a liquid 21b which may contain the object 21a to be observed. When the liquid 21b contain the object 21a to be observed, the object 21a to be observed is mounted on the surface of the stage portion 12 or above the surface of the stage portion 12. In the present embodiment, the liquid 21b containing the object 21a to be observed of 400 μm is mounted on the surface of the stage portion 12 of the microscopic imaging device 10. For example, the microscopic imaging device 10 has an interval P between pixels 14 of 1 μm and a viewing angle θ of the microlens 13 of 10 deg, and has a 10M sensor having 1000×1000 pixels 14 formed in the sensor unit 22 of the solid-state imaging device 11. It is noted that, in FIG. 4A, the number of pixels 14 arranged in the sensor unit 22 will be omitted. Further, the sensor unit 22 illustrated in FIG. 4A is electrically connected to the logic circuit portion 19 provided on the semiconductor substrate around the sensor unit 22, and the solid-state imaging device 11 including the sensor unit 22 and the logic circuit portion 19 is electrically connected to a mounting board 24.

It is noted that, in this microscopic imaging device 10, the object 21a to be observed which is mounted so as to have a distance L from the top of the microlens 13 of not more than 2.84 μm (=1/(2×tan 10)) can be normally imaged, and the stage portion 12 has a thickness of less than 2.84 μm.

When the object 21a to be observed is mounted on the surface of the stage portion 12 or above the surface of the stage portion 12, the object 21a to be observed is mounted so that a distance L between the top of the microlens 13 and the object 21a to be observed is not more than a predetermined distance P/(2×tan θ), so that the microscopic imaging device 10 can normally image the object 21a to be observed. The solid-state imaging device 11 images the mounted object 21a to be observed, and the logic circuit portion 19 performs desired signal processing on the voltage signal (raw date) obtained by the imaging. Then, the logic circuit portion 19 outputs the voltage signal subjected to the signal processing as the image signal. It is noted that "desired signal processing" includes color correction processing, noise correction processing, and image quality correction processing on the voltage signal, excluding lens aberration correction processing and shading correction processing. Additionally, in the following description, "desired signal processing" also represents the similar signal processing to the above description.

Finally, the display unit 20 forms an image of the object 21a to be observed, based on the image signal output from the logic circuit portion 19, and displays the image thereon.

It is noted that, in the microscopic imaging device 10 according to the present embodiment and the observation system using the device, the object 21a to be observed is displayed at a magnification M determined by the size of the object 21a to be observed and the interval P between pixels 14. The magnification M is expressed by a formula: M=size of the object 21a to be observed/interval P between pixels 14. As described above, when the size of the object 21a to be observed is 400 μm, and the interval P between pixels 14 is 1 μm, the object 21a to be observed is displayed at a magnification M of 400.

According to the observation method using the microscopic imaging device 10, having been described above, complicated operation, such as adjustment of the observational optical system and full scan over the object to be observed, is not required, the whole of the object to be observed can be easily observed at a time by simply mounting the object to be observed on the stage portion 12 of the microscopic imaging device 10.

<Modification>

Figure 5:
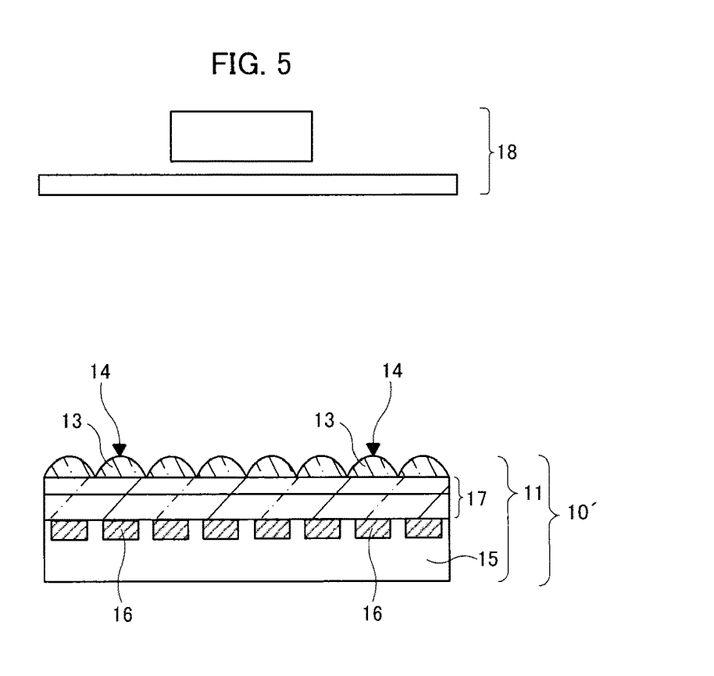
FIG. 5 is a cross-sectional view illustrating a microscopic imaging device used for an observation method according to a modification of the embodiment.

FIG. 5 is a cross-sectional view illustrating a microscopic imaging device used in an observation method according to a modification of the embodiment. As illustrated in FIG. 5, a microscopic imaging device 10' may not include the stage portion 12 on which the object to be observed can be mounted. Even with the microscopic imaging device 10' without including the stage portion 12, the object to be observed which is mounted within the predetermined distance L from the top of the microlens 13 can be normally imaged, similarly to the microscopic imaging device 10.

Figure 6A:
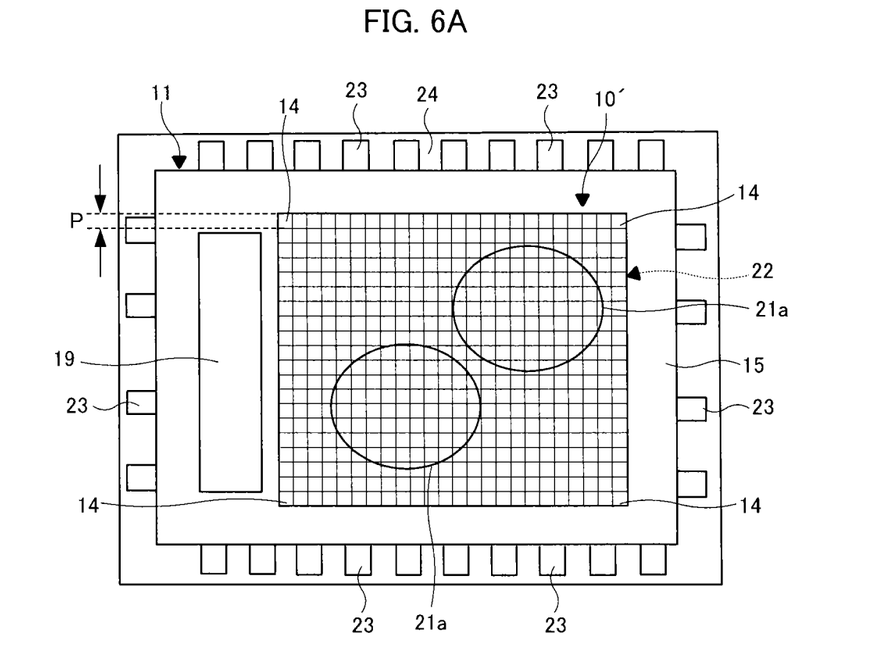
FIG. 6A is a top view of the microscopic imaging device according to the modification, the microscopic imaging device having microlenses on which an object to be observed is mounted.
Figure 6B:
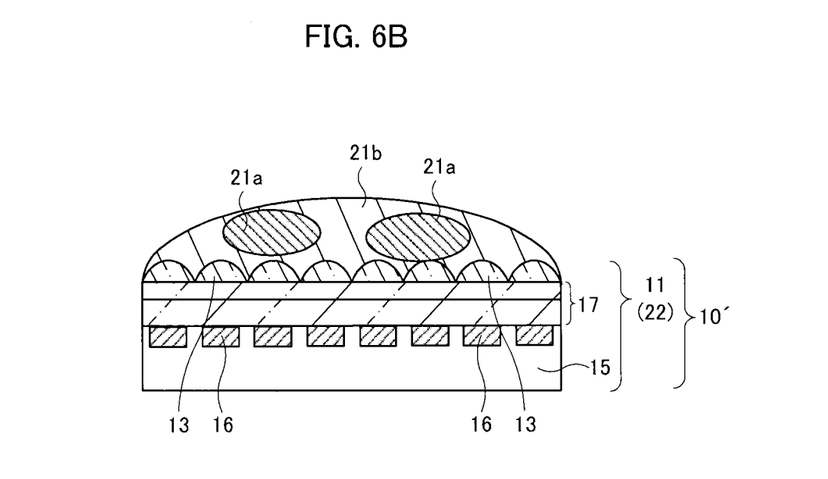
FIG. 6B is a partial cross-sectional view of FIG. 6A.

As illustrated in FIGS. 6A and 6B, an observation method using the microscopic imaging device 10' is similar to the observation method using the microscopic imaging device 10, except for mounting the liquid 21b which may contain the object 21a to be observed as the specimen on the plurality of microlenses 13 of the microscopic imaging device 10'. Accordingly, detailed description of the observation method using the microscopic imaging device 10' will be omitted. In the method, when the liquid 21b contain the object 21a to be observed, the object 21a to be observed is mounted on the microlens 13 or above the microlens 13.

In the observation method using the microscopic imaging device 10' having described above, the whole of the object to be observed can be easily observed at a time, similarly to the observation method using the microscopic imaging device 10.

Further, according to the observation method using the microscopic imaging device 10', the liquid 21b containing the object 21a to be observed as the specimen is directly mounted on the microlenses 13, so that the object 21a to be observed which exists farther from the microlens 13 of the microscopic imaging device 10' can be observed.

The observation methods using the microscopic imaging device 10 and 10' having been described above can be applied to various fields. Exemplary application of the methods will be described below.

<First Application>

Figure 7:
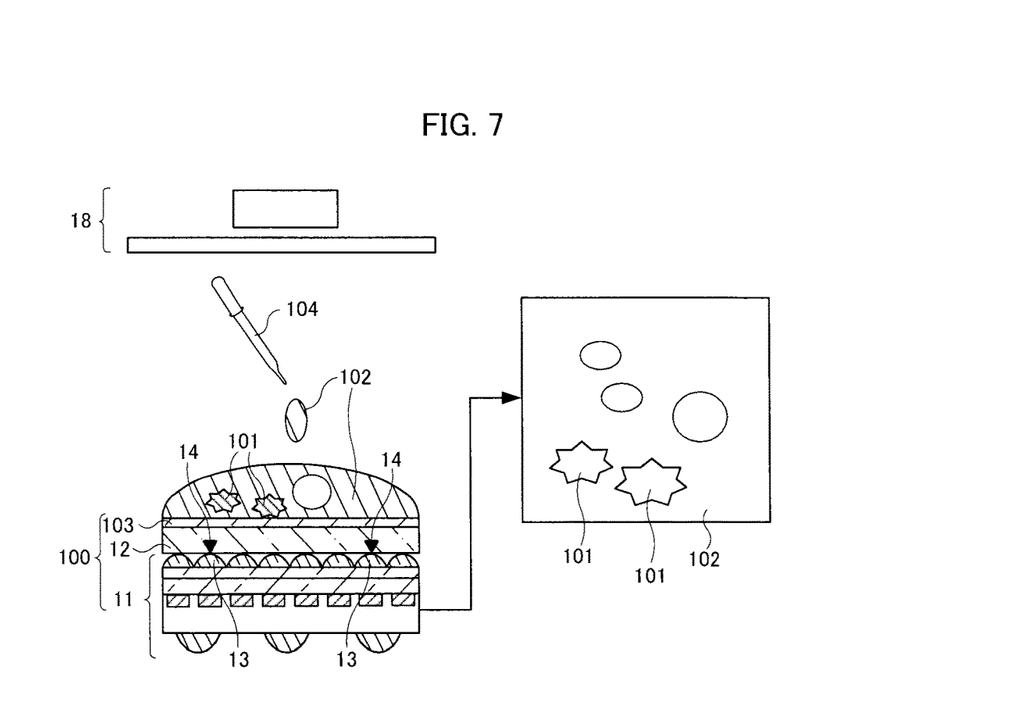
FIG. 7 is a diagram illustrating an observation method according to a first application.

FIG. 7 is a diagram illustrating an observation method according to a first application. A microscopic imaging device 100 shown in FIG. 7 includes the solid-state imaging device 11, the stage portion 12, and an insulation sheet 103 which is disposed on the surface of the stage portion 12. As illustrated in FIG. 7, the method using the microscopic imaging device 100 represents an exemplary application of the observation method according to the embodiment, to a biotechnology field. As illustrated in FIG. 7, according to the microscopic imaging device 100 and the observation system using the microscopic imaging device 100, a cancer cell 101 can be observed by dropping a liquid 102 containing the cancer cell 101 as a specimen on the insulation sheet 103 of the microscopic imaging device 100. This method will be described below.

First, for example, the microscopic imaging device 100 which is formed by disposing the insulation sheet 103 on the surface of the stage portion 12 is disposed under the desired light source 18, as illustrated in FIG. 7. For example, the microscopic imaging device 100 has an interval P between pixels 14 of 1 μm and a viewing angle θ of the microlens 13 of 10 deg, and has a 10M sensor having 1000×1000 pixels 14 formed in the sensor unit 22 of the solid-state imaging device 11. The insulation sheet 103 is disposed so as to suppress a short circuit of a plurality of wires 23 (FIG. 4A) provided around the stage portion 12 on the sensor unit 22, the short circuit caused by the liquid 102 dropped onto the surface of the stage portion 12 later.

In this microscopic imaging device 100, the object to be observed which is mounted to have a distance L from the top of the microlens 13 of not more than 2.84 μm can be imaged. Accordingly, in consideration of a thickness of the insulation sheet 103, the stage portion 12 has a thickness of less than 2.84 μm.

Next, as the specimen, the liquid 102 which may contain the cancer cell 101, as the object to be observed, is dropped on the insulation sheet 103, for example, using a dropping device 104 such as a pipette, and therefore the liquid 102 which may contain the cancer cell 101 as the specimen is mounted on the insulation sheet 103 (above the microlens 13). When the liquid 102 contain the cancer cell 101, the cancer cell 101 is mounted on the insulation sheet 103 or above the insulation sheet 103.

Then, when the liquid 102 containing the cancer cell 101 is mounted on the insulation sheet 103, the solid-state imaging device 11 images the liquid 102 containing the cancer cell 101, the liquid 102 having been mounted on the stage portion 12, and the logic circuit portion 19 (FIG. 3) performs the desired signal processing on the voltage signal (raw date) obtained by the imaging. Thereafter, the voltage signal subjected to the signal processing is output as the image signal.

Lastly, the display unit 20 (FIG. 3) forms an image of the liquid 102 containing the cancer cell 101 based on the image signal output from the logic circuit portion 19 (FIG. 3), and displays the image as illustrated in FIG. 7.

As described above, the cancer cell 101 can be observed.

<Modification of First Application>

Figure 8:
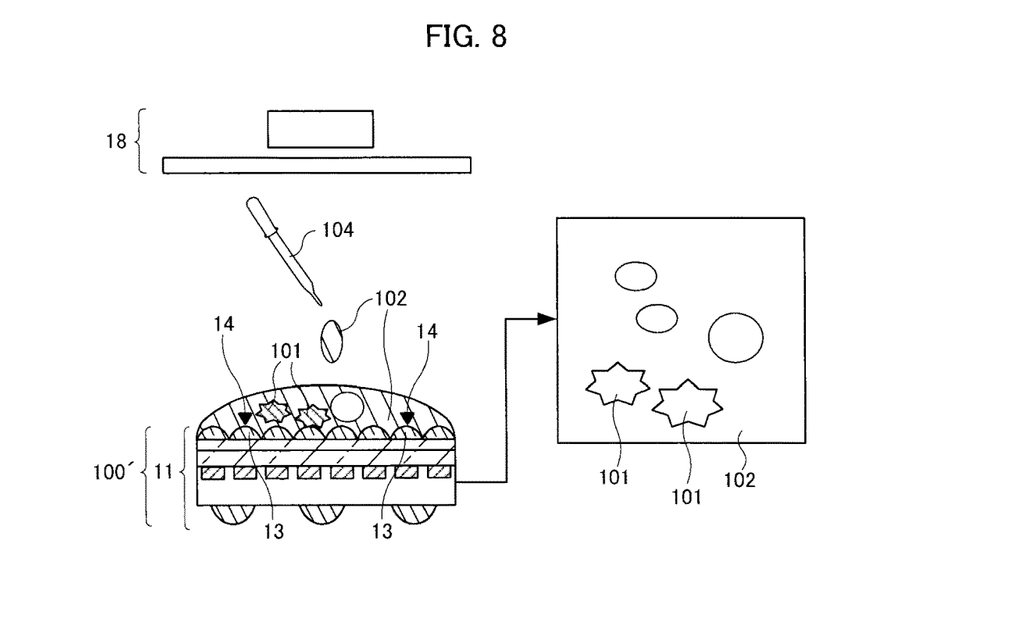
FIG. 8 is a diagram illustrating an observation method according to a modification of the first application.

FIG. 8 is a diagram illustrating an observation method according to a modification of the first application.

A microscopic imaging device 100' shown in FIG. 8 includes the solid-state imaging device 11, and doesn't include the stage portion 12 and the insulation sheet 103. As illustrated in FIG. 8, the method using the microscopic imaging device 100' is an exemplary application of the observation method according to the modification of the embodiment, to the biotechnology field. As illustrated in FIG. 8, according to the microscopic imaging device 100' and the observation system using the microscopic imaging device 100', the cancer cell 101 can be observed by dropping the liquid 102 which may contain the cancer cell 101 as the specimen on the microlenses 13 of the microscopic imaging device 100'. It is noted that details of the method is similar to that of the observation method according to the first application. Accordingly, detailed description of the observation method according to the modification of the first application will be omitted. In the method, when the liquid 102 contain the cancer cell 101, the cancer cell 101 is mounted on the microlenses or above the microlenses 13.

Even if the observation method according to the modification of the first application is employed, the cancer cell 101 can be observed, similarly to the observation method according to the first application.

Further, according to the observation method according to the modification of the first application, the cancer cell 101 existing farther from the microlens 13 can be observed, compared to the observation method according to the first application.

<Second Application>

Figure 9:
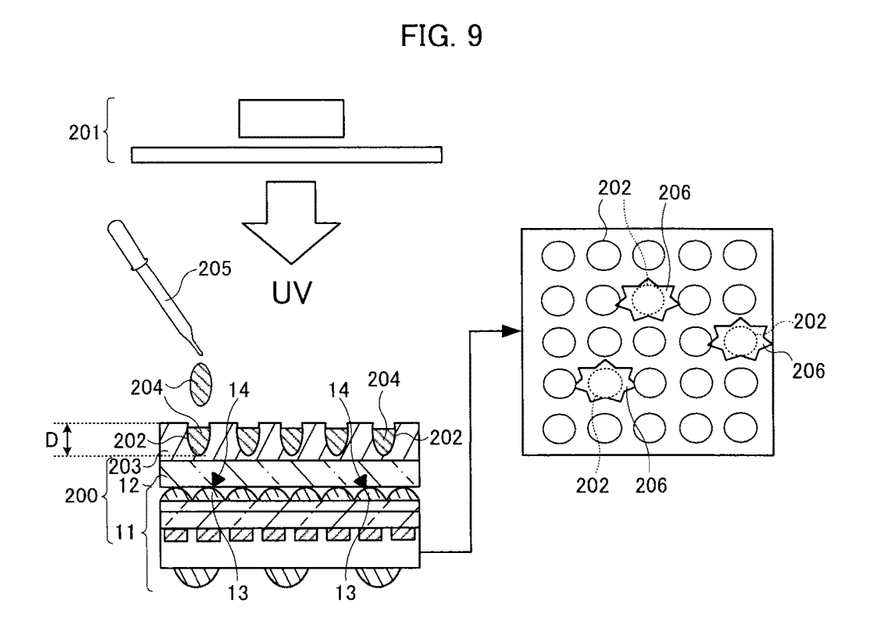
FIG. 9 is a diagram illustrating an observation method according to a second application.

FIG. 9 is a diagram illustrating an observation method according to a second application. A microscopic imaging device 200 shown in FIG. 9 includes the solid-state imaging device 11, the stage portion 12, and an examination container 203 which is disposed on the surface of the stage portion 12. As illustrated in FIG. 9, the method using the microscopic imaging device 200 is a method of applying the observation method according to the present embodiment to the biotechnology field. As illustrated in FIG. 9, in the microscopic imaging device 200 and the observation system using the microscopic imaging device 200, a drug reacting with an antibody to be detected is previously mounted on the surface of the stage portion 12, using the examination container 203. Further, a UV (ultraviolet) light source 201 is used as the light source. The presence or absence of the antibody can be observed by observing a fluorescence emission which caused by reaction between the antibody and the drug. This method will be described below.

First, for example, the microscopic imaging device 200 which is formed by disposing the examination container 203 having a plurality of recessed portions 202 on the surface of the stage portion 12 is disposed under the UV light source 201. For example, the microscopic imaging device 200 has an interval P between pixels 14 of 1 μm and a viewing angle θ of the microlens 13 of 10 deg, and has a 10M sensor having 1000×1000 pixels 14 formed in the sensor unit 22 of the solid-state imaging device 11. The number of recessed portions 202 in the examination container 203 is a matrix of approximately 10×10 over the sensor unit 22, and the drug reacting with an antibody to be detected, and emitting fluorescence by being irradiated with UV light is previously applied to the inside of the recessed portion 202.

In this microscopic imaging device 200, the object to be observed which is mounted to have a distance L from the top of the microlens 13 of not more than 2.84 μm can be imaged. Accordingly, the microscopic imaging device 200 is provided so that the sum of the thickness of the stage portion 12 and the thickness of the examination container 203 excluding a portion corresponding to the recessed portion 202 is not more than 2.84 μm. Accordingly, each recessed portion 202 of the examination container 203 extends from a surface of the examination container 203 in a thickness direction within a range not more than P/(2×tan θ). That is, each recessed portion 202 has a depth D of less than P/(2×tan θ).

Next, a liquid 204 which may contain the antibody being the object to be observed as a specimen is dropped in each recessed portion 202 of the examination container 203, using a dropping device 205 such as a pipette, and therefore the liquid 204 which may contain the antibody as the specimen is mounted above the stage portion 12 (above the microlens 13).

Next, when the liquid 204 which may contain the antibody is mounted above the stage portion 12, the antibody contained in the liquid 204 reacts with the drug applied to the inside of the recessed portion 202. In addition, UV light is applied from above. Accordingly, the inside of the recessed portion 202 containing the antibody emits fluorescence 206. The solid-state imaging device 11 images the emitted fluorescence 206, and the logic circuit portion 19 (FIG. 3) performs the desired signal processing on the voltage signal (raw date) obtained by the imaging. Thereafter, the voltage signal subjected to the signal processing is output as the image signal.

Lastly, the display unit 20 (FIG. 3) forms an image of the fluorescence 206 based on the image signal output from the logic circuit portion 19 (FIG. 3), and displays the image thereon as illustrated in FIG. 9.

As described above, the presence or absence of the antibody can be observed.

<Modification of Second Application>

Figure 10:
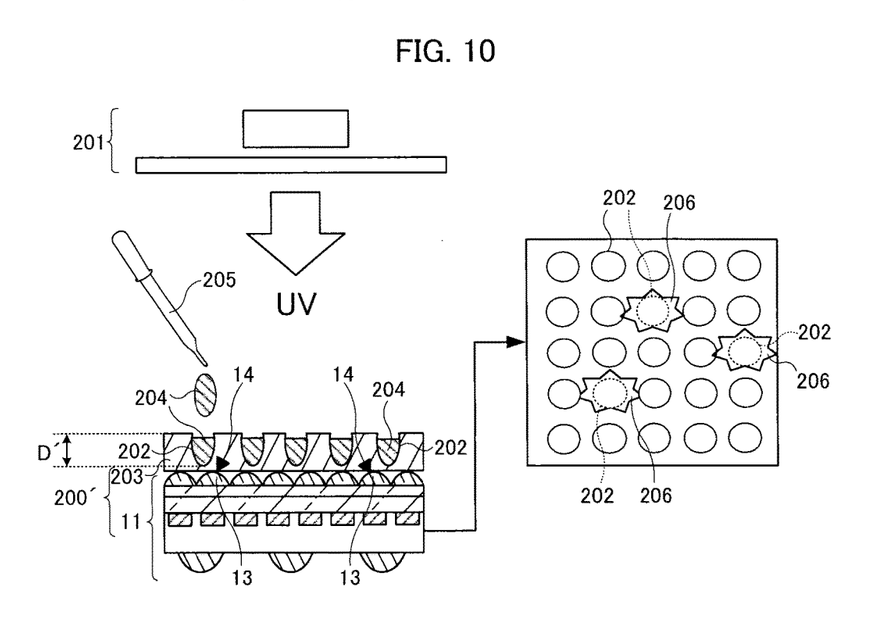
FIG. 10 is a diagram illustrating an observation method according to a modification of the second application.

FIG. 10 is a diagram illustrating an observation method according to a modification of the second application. A microscopic imaging device 200' shown in FIG. 10 includes the solid-state imaging device 11 and the examination container 203 which is disposed on the microlens 13, and doesn't include the stage portion 12. As illustrated in FIG. 10, the method using the microscopic imaging device 200' is a method of applying the observation method according to the modification of the embodiment to the biotechnology field. As illustrated in FIG. 10, in the microscopic imaging device 200' and the observation system using the microscopic imaging device 200', the drug reacting with the antibody to be detected is previously mounted on the microlenses 13 of the microscopic imaging device 200', using the examination container 203. Further, a UV (ultraviolet) light source 201 is used as the light source. The presence or absence of the antibody can be observed by observing a fluorescence emission which caused by reaction between the antibody and the drug. Each recessed portion 202 of the examination container 203 extends from the surface of the examination container 203 in a thickness direction within a range not more than $P/(2 \times \tan \theta)$. That is, each recessed portion 202 has a depth D' of less than $P/(2 \times \tan \theta)$. However, the microscopic imaging device 200' does not have the stage portion 12, so that the depth D' of each recessed portion 202 can be increased, compared with the depth D of each recessed portion 202 of the examination container 203 formed in the microscopic imaging device 200. It is noted that details of the method is similar to that of the observation method according to the second application. Accordingly, detailed description of the observation method according to the modification of the second application will be omitted. In the method, when the liquid 204 which may contain the antibody being the object to be observed as the specimen is dropped in each recessed portion 202 of the examination container 203, the liquid 204 which may contain the antibody as the specimen is mounted above the microlens 13.

Even if the observation method according to the modification of the second application is employed, the presence or absence of the antibody can be observed, similarly to the observation method according to the second application.

Further, according to the observation method according to the modification of the second application, the depth D' of each recessed portion 202 of the examination container 203 can be increased, compared with the observation method according to the second application. Accordingly, a larger amount of liquid 204 can be examined at a time, and the frequency of examination can be reduced.

<Third Application>

Figure 11:
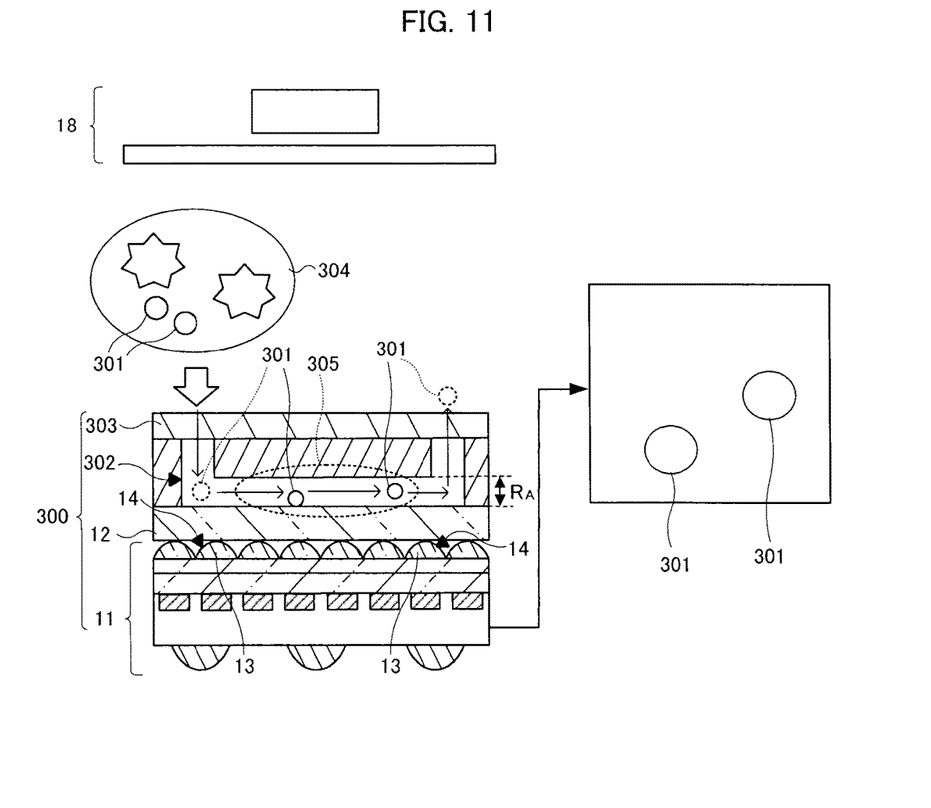
FIG. 11 is a diagram illustrating an observation method according to a third application.

FIG. 11 is a diagram illustrating an observation method according to a third application. A microscopic imaging device 300 shown in FIG. 11 includes the solid-state imaging device 11, the stage portion 12, a path 302 which is disposed on the surface of the stage portion 12 and is able to circulate a particulate matters 301 such as so-called PM 2.5, and a filter 303 which is provided at an inlet and an outlet of the path 302 and is able to pass the particulate matter 301. The path 302 is provided so that the surface of the stage portion 12 is exposed in the path 302. As illustrated in FIG. 11, the method using the microscopic imaging device 300 is a method of applying the observation method according to the present embodiment to an environmental field. As illustrated in FIG. 11, in the microscopic imaging device 300 and the observation system using the microscopic imaging device 300, the particulate matter 301 can be observed by passing through the particulate matter 301 into the path 302. This method will be described below.

First, for example, as illustrated in FIG. 11, the microscopic imaging device 300 having the path 302 and the filter 303 is disposed under the desired light source 18. For example, the microscopic imaging device 300 has an interval P between pixels 14 of 1 μm and a viewing angle θ of the microlens 13 of 10 deg, and has a 10M sensor having 1000×1000 pixels 14 formed in the sensor unit 22 of the solid-state imaging device 11.

In this microscopic imaging device 300, the object to be observed which is mounted to have a distance L from the top of the microlens 13 of not more than 2.84 μm can be imaged. Accordingly, the microscopic imaging device 300 is provided so that the sum of the thickness of the stage portion 12 and a diameter $R_A$ of the path 302 is not more than 2.84 μm. Accordingly, the path 302 has a diameter $R_A$ of less than $P/(2 \times \tan \theta)$.

Next, a gas 304 which may contain the particulate matter 301 as a specimen is circulated in the path 302 through the filter 303. When the gas 304 contain the particulate matter 301, the particulate matter 301 is mounted on the stage portion 12 or above the stage portion 12 (above the microlens 13).

Next, when the solid-state imaging device 11 is caused to keep imaging an observation area 305 which is formed by an area on the stage portion 12 and an area above the stage portion 12, the solid-state imaging device 11 images the particulate matter 301 reaching the observation area 305, and the logic circuit portion 19 (FIG. 3) performs the desired signal processing on the voltage signal (raw date) obtained by the imaging. Thereafter, the voltage signal subjected to the signal processing is output as the image signal.

Lastly, the display unit 20 (FIG. 3) forms an image of the particulate matter 301 based on the image signal output from the logic circuit portion 19 (FIG. 3), and displays the image thereon as illustrated in FIG. 11.

As described above, the particulate matter 301 can be observed.

<Modification of Third Application>

Figure 12:
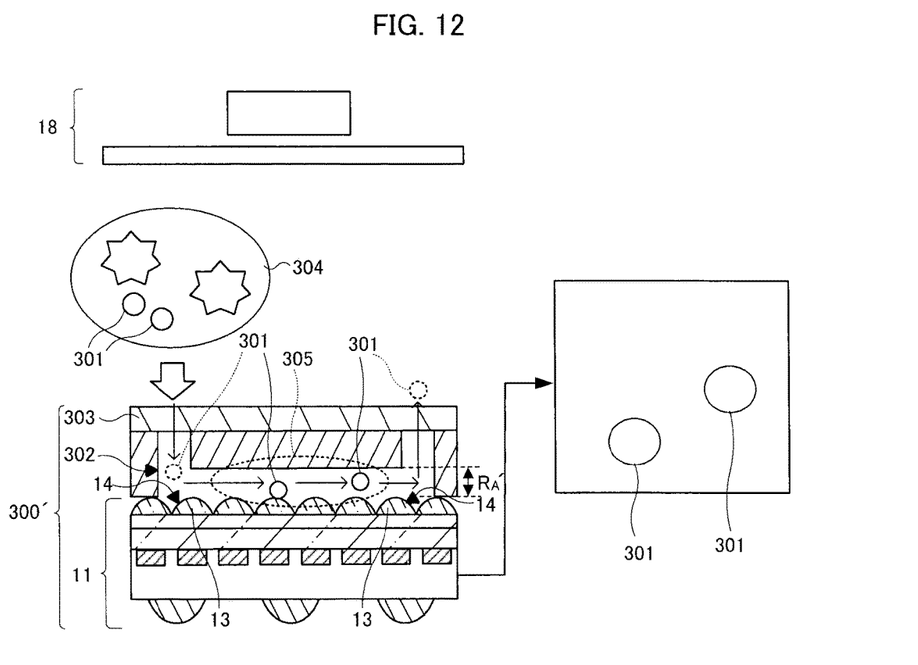
FIG. 12 is a diagram illustrating an observation method according to a modification of the third application.

FIG. 12 is a diagram illustrating an observation method according to a modification of the third application.

A microscopic imaging device 300' shown in FIG. 12 includes the solid-state imaging device 11, the path 302, and the filter, and doesn't include the stage portion 12. As illustrated in FIG. 12, the method using the microscopic imaging device 300' is a method of applying the observation method according to the modification of the embodiment to the environmental field. As illustrated in FIG. 12, in the microscopic imaging device 300' and the observation system using the microscopic imaging device 300', the path 302 for circulating the particulate matter 301 is provided on the microlenses 13 of the microscopic imaging device 300' so that the microlenses 13 are exposed in the path 302. The path 302 has a diameter $R_A'$ of less than $P/(2 \times \tan \theta)$. However, the microscopic imaging device 300' does not have the stage portion 12, so that the diameter $R_A'$ of the path 302 can be increased, compared with the diameter $R_A$ of the path 302 on the microscopic imaging device 300. The particulate matter 301 can be observed by passing through the gas 304 which may contain the particulate matter 301 as the specimen into the path 302 and mounting the particulate matter 301 on the microlenses 13 or above the microlenses 13. It is noted that details of the method is similar to that of the observation method according to the third application. Accordingly, detailed description of the observation method according to the modification of the third application will be omitted.

Even if the observation method according to the modification of the third application is employed, the particulate matter 301 can be observed, similarly to the observation method according to the third application.

Further, according to the observation method according to the modification of the third application, the diameter $R_A'$ of the path 302 provided on the microscopic imaging device 300' can be increased, compared with the observation method according to the third application. Accordingly, a larger amount of the gas 304 can be examined at a time, and a time for examination can be reduced.

<Fourth Application>

Figure 13:
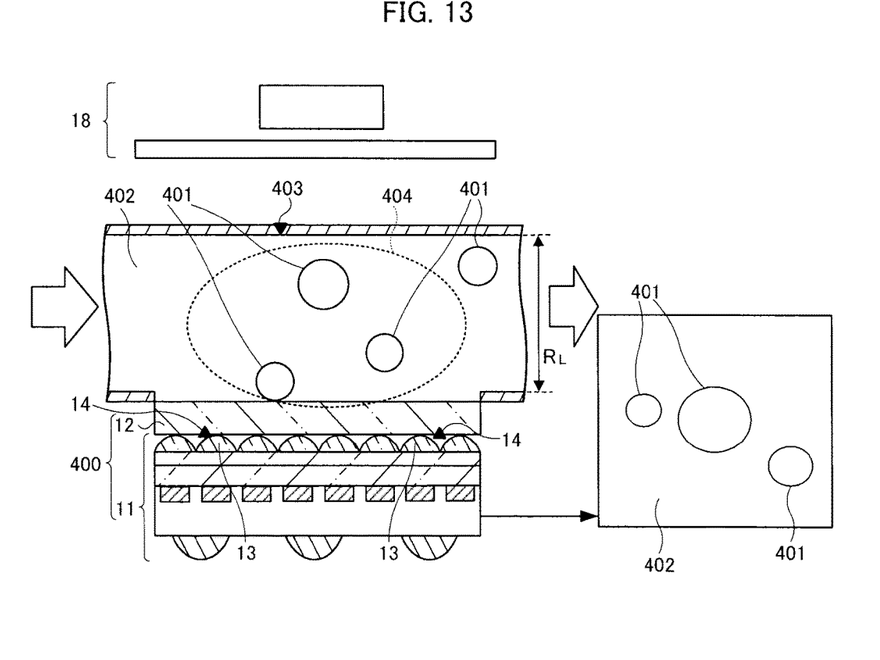
FIG. 13 is a diagram illustrating an observation method according to a fourth application.

FIG. 13 is a diagram illustrating an observation method according to a fourth application. A microscopic imaging device 400 shown in FIG. 13 includes the solid-state imaging device 11 and the stage portion 12. As illustrated in FIG. 13, the method using the microscopic imaging device 400 is a method of applying the observation method according to the embodiment to the environmental field. As illustrated in FIG. 13, according to the microscopic imaging device 400 and the observation system using the microscopic imaging device 400, the microscopic imaging device 400 is previously provided to a flow path 403 for circulating water 402 which may contain a contaminant 401, such as microorganisms or algae, as a specimen, so that the surface of the stage portion 12 is exposed in the flow path 403. When the water 402 contain the contaminant 401, the contaminant 401 can be observed by passing through the water 402 which may contain the contaminant 401 as the specimen into the flow path 403. This method will be described below.

First, as illustrated in FIG. 13, the microscopic imaging device 400 is provided to the flow path 403 so that the surface of the stage portion 12 of the microscopic imaging device 400 is exposed in the flow path 403. For example, the microscopic imaging device 400 has an interval P between pixels 14 of 1 μm and a viewing angle θ of the microlens 13 of 10 deg, and has a 10M sensor having 1000×1000 pixels 14 formed in the sensor unit 22 of the solid-state imaging device 11. The microscopic imaging device 400 having such a configuration is disposed under the desired light source 18.

In this microscopic imaging device 400, the object to be observed which is mounted to have a distance L from the top of the microlens 13 of not more than 2.84 μm can be imaged. Accordingly, the microscopic imaging device 400 is provided so that the sum of the thickness of the stage portion 12 and a diameter $R_L$ of the path 403 is not more than 2.84 μm. Accordingly, the flow path 403 has a diameter $R_L$ of less than P/(2×tan θ).

Next, the water 402 which may contain the contaminant 401 as the specimen is circulated in the flow path 403. When the water 402 contain the contaminant 401, the contaminant 401 is mounted on the stage portion 12 or above the stage portion 12 (above the microlens 13).

Next, when the solid-state imaging device 11 is caused to keep imaging an observation area 404 which is formed by an area on the stage portion 12 and an area above the stage portion 12, the solid-state imaging device 11 images the contaminant 401 reaching the observation area 404, and the logic circuit portion 19 (FIG. 3) performs the desired signal processing on the voltage signal (raw date) obtained by the imaging. Thereafter, the voltage signal subjected to the signal processing is output as the image signal.

Figure 14:
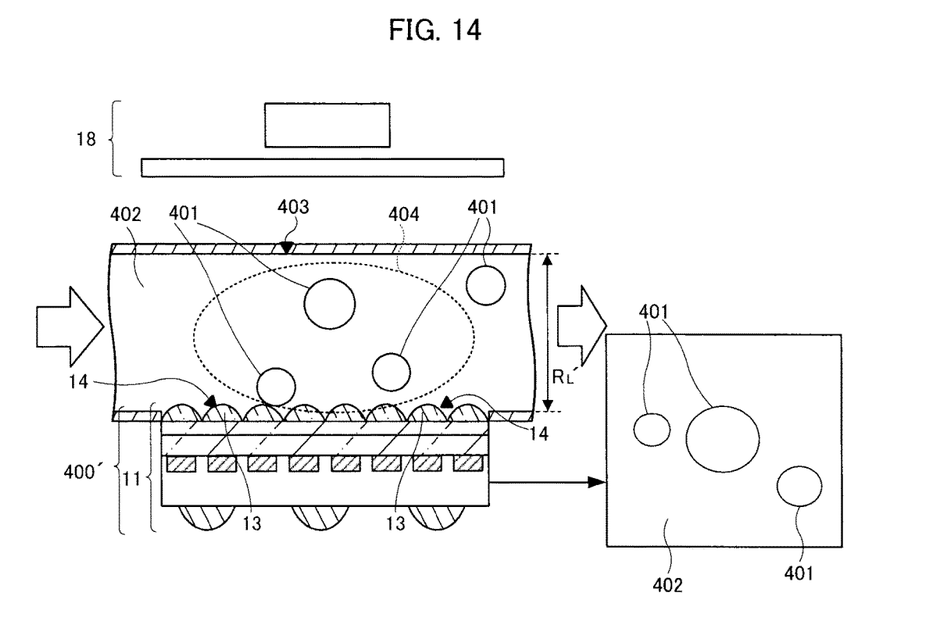
FIG. 14 is a diagram illustrating an observation method according to a modification of the fourth application.

Lastly, the display unit 20 (FIG. 3) forms an image of the contaminant 401 based on the image signal output from the logic circuit portion 19 (FIG. 3), and displays the image thereon as illustrated in FIG. 14.

As described above, the contaminant 401 can be observed.

<Modification of Fourth Application>

FIG. 14 is a diagram illustrating an observation method according to a modification of the fourth application. A microscopic imaging device 400' shown in FIG. 14 includes the solid-state imaging device 11, and doesn't include the stage portion 12. As illustrated in FIG. 14, the method using the microscopic imaging device 400' is a method of applying the observation method according to the modification of the embodiment to the environmental field. As illustrated in FIG. 14, according to the microscopic imaging device 400' and the observation system using the microscopic imaging device 400', the microscopic imaging device 400' is previously provided to the flow path 403 for circulating water 402 which may contain the contaminant 401, such as microorganisms or algae, as the specimen, so that the microlenses 13 are exposed in the flow path 403. The flow path 403 has a diameter $R_L'$ of less than P/(2×tan θ). However, the microscopic imaging device 400' does not have the stage portion 12, so that the diameter $R_L'$ of the flow path 403 can be increased, compared with the diameter $R_L$ of the flow path 403 to which the microscopic imaging device 400 is provided. The contaminant 401 can be observed by passing through the water 402 which may contain the contaminant 401 as the specimen into the flow path 403 and mounting the particulate matter 301 on the microlenses 13 or above the microlenses 13. It is noted that details of the method is similar to that of the observation method according to the fourth application. Accordingly, detailed description of the observation method according to the modification of the fourth application will be omitted.

Even if the observation method according to the modification of the fourth application is employed, the contaminant 401 can be observed, similarly to the observation method according to the fourth application.

Further, according to the observation method according to the modification of the fourth application, the diameter $R_L'$ of the flow path 403, to which the microscopic imaging device 400' is provided, can be increased, compared with the observation method according to the fourth application. Accordingly, a larger amount of water 402 can be examined at a time, and a time for examination can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, in the above embodiment, applications, and their modifications, the solid-state imaging device 11 may be a front-side illumination type or a back-side illumination type.

Further, in the above-mentioned applications, the exemplary applications of the observation methods according to the embodiment to the biotechnology field and the environmental field has been described, but a field to which the observation method according to the embodiment is to be applied is also not limited. For example, when it is desired to observe an object to be observed which is larger than 0.2 nm (object to be observed which has a size observable under an optical microscope), the present embodiment can be applied. The solid-state imaging device can be improved in interval between pixels, design of microlens, the light source, or the like to observe even an object to be observed which is smaller than 0.2 nm (object to be observed which has a size observable under an electronic microscope), and upon observation of such an extremely minute object to be observed, the present embodiment can be also applied.

What is claimed is:

1. An observation method using a microscopic imaging device which has a solid-state imaging device having a plurality of pixels arranged at predetermined intervals, each of the pixels including a microlens configured to collect light, a light receiving unit configured to receive the light collected by the microlens, and a stage portion provided on the microlenses of the solid-state imaging device on which an object to be observed is mounted on or above, comprising:

mounting the object to be observed on the microlenses or above the microlenses by disposing a specimen containing the object to be observed on the microscopic imaging device; and imaging the object to be observed, mounted on the microlenses or above the microlenses by the solid-state imaging device, wherein, the microscopic imaging device does not include an observational optical system for focusing, magnification, and reduction, and when an interval between the pixels is denoted by P, and a viewing angle of the microlens is denoted by θ, the object to be observed is mounted on the microlenses or above the microlenses so that a distance between one of the microlenses and the object to be observed is not more than $P/(2 \times \tan \theta)$.

2. The observation method using a microscopic imaging device according to claim 1, the observation method further comprising:

obtaining a voltage signal by imaging the object to be observed by the solid-state imaging device, obtaining an image signal by performing desired signal processing on the voltage signal, the desired signal processing including color correction processing, noise correction processing, and image quality correction processing, excluding lens aberration correction processing and shading correction processing, and displaying an image of the object to be observed based on the image signal.

3. The observation method using a microscopic imaging device according to claim 1, wherein the microscopic imaging device includes a path provided on the microlenses, the path configured to expose the microlenses in the path, and a filter provided at an inlet of the path, the filter configured to pass the object to be observed, and the object to be observed is mounted on the microlenses or above the microlenses by circulating the specimen in the path through the filter.

4. The observation method using a microscopic imaging device according to claim 1, wherein the microscopic imaging device is provided to a flow path so that the microlenses is exposed in the flow path, and the object to be observed is mounted on the microlenses or above the microlenses by circulating the specimen in the flow path.

5. The observation method using a microscopic imaging device according to claim 1, the observation method further comprising:

obtaining a voltage signal by imaging the object to be observed by the solid-state imaging device, obtaining an image signal by performing desired signal processing on the voltage signal, the desired signal processing including color correction processing, noise correction processing, and image quality correction processing, excluding lens aberration correction processing and shading correction processing, and displaying an image of the object to be observed based on the image signal.

6. The observation method using a microscopic imaging device according to claim 1, wherein the microscopic imaging device has an insulation sheet on a surface of the stage portion, and the object to be observed is mounted on the insulation sheet or above the insulation sheet.

7. The observation method using a microscopic imaging device according to claim 1, wherein the microscopic imaging device has, on a surface of the stage portion, an examination container having a plurality of recessed portions provided to extend from a surface of the examination container in a thickness direction, and the object to be observed is mounted above the stage portion by disposing the specimen in each of the recessed portions.

8. The observation method using a microscopic imaging device according to claim 1, wherein the microscopic imaging device includes a path provided on a surface of a surface of the stage portion, the path configured to expose the surface of the stage portion in the path, and a filter provided at an inlet of the path, the filter configured to pass the object to be observed, and the object to be observed is mounted on stage portion or above the stage portion by circulating the specimen in the path through the filter.

9. The observation method using a microscopic imaging device according to claim 1, wherein the microscopic imaging device is provided to a flow path so that the stage portion is exposed in the flow path, and the object to be observed is mounted on the stage portion or above the stage portion by circulating the specimen in the flow path.

10. An observation method using a microscopic imaging device which has a solid-state imaging device having a plurality of pixels arranged at predetermined intervals, each of the pixels including a microlens configured to collect light, a light receiving unit configured to receive the light collected by the microlens, and, on the microlenses, an examination container having a plurality of recessed portions provided to extend from a surface of the examination container in a thickness direction, and on which an object to be observed is mounted above the microlenses by disposing the specimen in each of the recessed portions, comprising;

mounting the object to be observed on the microlenses or above the microlenses by disposing a specimen containing the object to be observed on the microscopic imaging device; and     imaging the object to be observed, mounted on the microlenses or above the microlenses by the solid-state imaging device,     wherein, the microscopic imaging device does not include an observational optical system for focusing, magnification, and reduction, and     when an interval between the pixels is denoted by P, and a viewing angle of the microlens is denoted by $\theta$, the object to be observed is mounted on the microlenses or above the microlenses so that a distance between one of the microlenses and the object to be observed is not more than $P/(2 \times \tan \theta)$.

11. The observation method using a microscopic imaging device according to claim 10, the observation method further comprising:

obtaining a voltage signal by imaging the object to be observed by the solid-state imaging device,     obtaining an image signal by performing desired signal processing on the voltage signal, the desired signal processing including color correction processing, noise correction processing, and image quality correction processing, excluding lens aberration correction processing and shading correction processing, and     displaying an image of the object to be observed based on the image signal.

12. The observation method using a microscopic imaging device according to claim 10,     wherein the microscopic imaging device has a stage portion provided on the microlenses of the solid-state imaging device, and an insulation sheet on a surface of the stage portion,     the object to be observed is mounted on the insulation sheet or above the insulation sheet.

\* \* \* \* \*